(12) United States Patent
Badawy

(10) Patent No.: US 8,003,704 B2
(45) Date of Patent: Aug. 23, 2011

(54) METHODS AND COMPOSITIONS FOR THE TREATMENT OF ALCOHOLISM AND ALCOHOL DEPENDENCE

(76) Inventor: Abdulla Abu-Bakr Badawy, Cardiff (GB)

( * ) Notice: Subject to any disclaimer, the term of this patent is extended or adjusted under 35 U.S.C. 154(b) by 1630 days.

(21) Appl. No.: 10/312,733

(22) PCT Filed: Jul. 2, 2001

(86) PCT No.: PCT/GB01/02930
§ 371 (c)(1),
(2), (4) Date: Aug. 26, 2003

(87) PCT Pub. No.: WO02/02091
PCT Pub. Date: Jan. 10, 2002

(65) Prior Publication Data
US 2008/0076796 A1    Mar. 27, 2008

(30) Foreign Application Priority Data

Jun. 30, 2000 (GB) .................................. 0016056.4
Jul. 15, 2000 (GB) .................................. 0017345.0

(51) Int. Cl.
*A61K 31/136* (2006.01)
*A61K 31/045* (2006.01)
*A61K 31/05* (2006.01)
*A61K 31/13* (2006.01)
*A61K 31/135* (2006.01)
*A61K 31/185* (2006.01)
*A61K 31/19* (2006.01)
*A61K 31/192* (2006.01)
*A61K 31/195* (2006.01)

(52) U.S. Cl. ........ 514/741; 514/646; 514/724; 514/727; 514/728; 514/730; 514/731; 562/405; 562/433; 562/458

(58) Field of Classification Search .................. None
See application file for complete search history.

(56) References Cited

FOREIGN PATENT DOCUMENTS

| EP | 0 085 283 | | 8/1983 |
|---|---|---|---|
| WO | WO 97/17317 | * | 5/1997 |
| WO | WO 99/58124 | * | 11/1998 |
| WO | WO99/58124 | | 11/1999 |

OTHER PUBLICATIONS

Minaño, F. J. et al. (1989) Psychopharm. 98; 176-182.*
Collins, M. A., et al. (1976) Ann. NY Acad. Sci. 273; pp. 227-233.*
F.S. Messiha, "Possible Mechanism of Adverse Reaction Following Levodopa Plus Benserazide Treatment", Department of Pharmacology and Therapeutics and Department of Psychiatry, Texas Tech University School of Medicine, Lubbock, Texas, U.S.A. Br. J. Pharmac (1997), 60, 55-57. Received Aug. 3, 1976. Revised Dec. 7, 1976.

F.S. Messiha, "Voluntary Drinking of Ethanol by the Rat: Biogenic Amines and Possible Underlying Mechanism", Department of Pathology, Psychopharmacology Laboratory, Department of Psychiatry, Texas Tech University School of Medicine, Lubbock, Texas 79409. Received Apr. 10, 1978. Copyright 1978, Ankho International Inc.
European Search Report dated Sep. 22, 2004 in connection with EP 01 94 3689.
Silvestre J S et al: 'Comparison of effects of a range of 5-HT receptor modulators on consumption and preference for a sweetened ethanol solution in rats'. Journal of Psychopharmacology, Oxford University Press, GB. vol. 12, No. 2, 1998, pp. 168-176, XP008034697. ISSN: 0296-8811.
Pettinati H M: Use of serotonin selective pharmacotherapy in the treatment of alcohol dependence. Alcoholism: Clinical and experimental research, Williams and Wilkings, Baltimore MD, US. vol. 20, No. 7, Oct. 1996, pp. 23A-29A, XP008034700. ISSN: 0145-6008.
Baskina N F, Lapin I P: 'Alteration of alcohol selection in chronically drinking cats by tryptophan, its metabolites and by drugs modifying tryptophan metabolism' Farmakol. Toksicol., vol. 45, No. 1, 1982, pp. 70-76, XP008034780. Abstract.
Whitehouse L W, Paul C J, Thomas B H: 'Isoniazid-induced intolerance to ethanol in rabbit, guinea pig and rat' Biopharmaceutics and drug disposition, vol. 1, 1960, pp. 235-245.
Database Biosis Online, Biosciences Information Service, Philadelphia, PA, US; 1991. Lapin, I. P. et al., "Using kynurenines to prevent ethanol-induced disorders in the hole reflect of mice and rats". XP002297059. Database accession No. PREV199293011729; and Zhurnal Vshei Nrvoi Dyatel 'Nsti len IP Pavlova, vol. 41, No. 3, 1991, pp. 551-557, ISSN: 0044-4677.
Lapin I P et al: Antiethanol effects of indol-3.-ylpyruvic acid in mice. Alcohol and alcoholism, Pergamon, Oxford, GB. vol. 29, No. 3, May 1994, pp. 265-268, XP001030543. ISSN: 0735-0414.
Minano F J at al: Inhibition of brain dopa-decarboxylase by RO 4-4602 infused ICV blocks alcohol drinking induced in rats by cyanamide' Pyschopharmacology, Springer Verlag, Berlin, DE. vol. 98, No. 2, 1989, pp. 176-182, XP008034777. ISSN: 0033-3158.
George D T et al: Buspirone treatment of alcoholism: Age of onset, and cerebrospinal fluid 5-hydroxyindolacetic acid and homovanillic acid concentrations, but not medication treatment, predict return to drinking'. Alcoholism: Clinical and experimental research, Williams and Wilkings, Baltimore, MD, US. vol. 23, No. 2, Feb. 1999 pp. 272-278, XP008034699. ISSN: 0145-6008.
Highley J D et al: 'Central nervous system serotonin and personality as variables contributing to excessive alcohol consumption in non-human primates'. Alcohol and alcoholism, Pergamon, Oxford, GB. vol. 34, No. 3, 1999, pp. 402-418, XPOO1199594. ISSN: 0735-0414.

(Continued)

Primary Examiner — Sharmila G. Landau
Assistant Examiner — Kevin S Orwig
(74) Attorney, Agent, or Firm — Young & Thompson

(57) ABSTRACT

Use is disclosed of (a) an AlDH-inhibitory amount of a Trp metabolite, or an analogue or derivative thereof or (b) a bioprecursor thereof, or (c) a potentiator of (a) and/or (b), in the preparation of a medicament for treating alcoholism and/or alcohol dependence.

4 Claims, No Drawings

OTHER PUBLICATIONS

N Ragusa et al., "Effects of Multi Vitamin Treatment on the Activity of Rat Liver Tryptophan Pyrrolase EC-1.13.11.11 During Ethanol Administration", vol. 3, No. 4, 1981, pp. 199-204, XP001030744, ISSN: 0300-8924, p. 200, left-hand column, paragraphs 2, 6, p. 202, left-hand column, paragraph 2, p. 203, right-hand column, paragraph 1.

"The Merck Index, 12th Edition", Merck & Co., Inc., Whitehouse Station, NJ, USA XP002180866, p. 1669, paragraph 9929, (1996).

"Martindale, The Extra Pharmacopeia, 30th Edition", The Pharmaceutical Press, London, UK, XP002180867, p. 273, middle column—p. 274, middle column, (1993).

Database Biosis (Online) Biosciences Information Service, Philadelphia, PA, US; 1994 Adell Albert et al:,"Increased alcohol intake in low alcohol drinking rats after chronic infusion of the beta-carboline harman into the hippocampus.", Database accession No. PREV199598055659, XP002180868 abstract & Pharmacology Biochemistry and Behavior, vol. 49, No. 4, 1994, pp. 949-953, ISSN: 0091-3057.

Allegri, G. et al:, "Studies on Tryptophan Metabolism in ethylism", Acta Vitaminol, Enzymol. (1975), 29(1-6), 169-73, XP001030523, p. 169, left-hand column, paragraph 1, p. 170, left-hand column, paragraph 3, figures 1-3, p. 172, left-hand column, line 2—p. 173, left-hand column, line 5.

* cited by examiner

METHODS AND COMPOSITIONS FOR THE TREATMENT OF ALCOHOLISM AND ALCOHOL DEPENDENCE

This invention relates to methods and compositions for the treatment of alcoholism and alcohol dependence, to compounds for use in such methods and compositions and such uses thereof.

BACKGROUND OF THE INVENTION

Treatment of alcoholism by aversion therapy involves the use of a drug known to inhibit the activity of the enzyme aldehyde dehydrogenase (AlDH; EC. 1.2.1.3 (International Union of Biochemistry and Molecular Biology (IUMB) nomenclature)) in the liver, thus leading to accumulation in the liver and hence blood of the toxic metabolite of alcohol or ethanol, namely acetadehyde, if the person drinks alcohol during such therapy. Currently, two AlDH inhibitors are used in aversion therapy, namely disulfiram (also known as Antabuse) and calcium cyanamide. Of these two aversion therapies, disulfiram is the preferred one, because of its longer duration of action which makes its administration and supervision much easier, although calcium cyanamide may have fewer side effects.

The toxicity of acetaldehyde manifests itself in a toxic reaction (the disulfiram-ethanol reaction or DER) involving symptoms such as sensation of heat, smell of acetaldehyde, facial flushing, conjunctival injection, palpitations, throbbing, hypotension (low blood pressure), cough, dyspnoea (difficulty of breathing), universal flush, headache, nausea, vomiting, sleepiness and, in severe cases, coma and death. The severity of the DER varies widely between individuals, presumably depending on individual tolerance to acetaldehyde, and how much acetaldehyde accumulates in any one person. The latter is, in turn, determined by how much alcohol is consumed and how much AlDH inhibition is achieved by disulfiram.

Disulfiram itself, however, has both undesirable and sometimes unwelcome serious side effects. Thus, among these side-effects are drowsiness, severe hypotension (low blood pressure), paresthesias (perverted sense of tingling, crawling, or burning of the skin, such as occurs in peripheral neuritis and spinal cord lesions), peripheral neuropathies, psychosis and hepatitis, all of which reduce markedly the rate of compliance with self-administration of the drug and, hence, its efficacy as an aversion therapy of alcoholism. Furthermore, even in subjects who comply with intake of tolerable doses of the drug, about one half develop the DER but the other half loses (does not experience) the deterrent property through which the drug exerts its action.

As regards calcium cyanamide, which is more widely used in Japan recent studies there have shown it to exert other equally unwelcome toxic effects, e.g. persistent liver dysfunction even with prolonged abstinence, and liver fibrosis and emergence of "ground glass" liver cells in those who relapse into drinking.

For these reasons, an alternative alcohol aversion therapy, using safer AlDH inhibitors that are free from the above undesirable side effects is a highly desirable goal and is the subject of this application.

As a result of studies conducted by the Applicants, the Applicants found a number of novel treatments for alcohol aversion therapy based on the tryptophan metabolic pathways. Tryptophan (Trp) is metabolised by at least four known pathways:

(1) the kynurenine-nicotinic acid pathway, the major pathway in the liver accounting for more than 90% of overall tryptophan metabolism and producing a variety of important metabolites;

(2) the serotonin pathway, which although of minor quantitative significance, is nevertheless of major importance in the central nervous system (CNS), because serotonin controls many important brain functions, such as mood, emotions, impulse control, appetite, the desire to drink alcohol, and other processes;

(3) the tryptamine or decarboxylation pathway, which is quantitatively more important than the serotonin pathway;

(4) the transamination pathway.

Accordingly, the present invention provides use of (a) an AlDH-inhibitory amount of a Trp metabolite, or an analogue or derivative thereof (as defined herein) or (b) a bioprecursor thereof (as defined herein), or (c) a potentiator of (a) and/or (b) (as defined herein), in the preparation of a medicament for treating alcoholism and/or alcohol dependence.

In the context of the present invention, the term 'tryptophan (or Trp) metabolite' encompasses both direct metabolites of Trp producible by the first stage in any of its metabolic pathways and indirect metabolites producible at further, downstream, stages of any of its metabolic pathways. The term 'bioprecursor' is well known to those skilled in the art and means any compound that metabolises in vivo to, in the case of the present invention, a Trp metabolite. Suitable bioprecursors may be selected from: Trp and AlDH non-inhibitory metabolites of Trp. The term 'AlDH non-inhibitory metabolites of Trp' means Trp metabolites that do not inhibit or only weakly inhibit (to an extent that would be considered therapeutically ineffective) AlDH.

The term 'potentiator' means an agent capable of potentiating such a Trp metabolite, whether directly or via a bioprecursor thereof. Such potentiating agents are capable of affecting the activity of a metabolic pathway, whereby an increase in the availability of an AlDH-inhibitory Trp metabolite is enabled. Such potentiation may be by any means, such as by enzymatic or catalytic means, by accentuation of favourable reaction conditions or increased amount of metabolic bioprecursor, or the like. Potentiation encompasses both increasing the presence of compounds or conditions to favour production of active Trp metabolites and inhibition of compounds or conditions that would otherwise inhibit or break down active Trp metabolites.

In particular, treatments according to this invention include:

(1) use of a tryptophan metabolite in general and one or more of the following in particular: 3-hydroxykynurenine, 3-hydroxyanthranilic acid, kynurenic acid and indol-3-ylpyruvic acid, or an analogue thereof, such as tryptophan metabolites normally absent a 3-hydroxy group which have been modified by insertion of a 3-hydroxy substituent, as an inhibitor of AlDH;

(2) use of a derivative in which the 3-hydroxy group of the tryptophan metabolite (1) is replaced by a nucleophilic group such as halo (eg chloro) and alkoxy, or other hydrophilic groups, or other substituent groups, such as lower ($C_{1-6}$) alkyl (eg methyl), or any of these group(s) substituted at one or more other position(s) (in addition to the 3-hydroxy group), as an AlDH inhibitor;

(3) use of an inhibitor of one or more enzyme(s) of the kynurenine-nicotinic acid pathway downstream of an AlDH-inhibitory Trp metabolite and, in particular, an inhibitor of kynureninase, to increase the levels of one or more of the tryptophan metabolites which inhibit AlDH activity; and/or (4) use of tryptophan in association with an inhibitor of one or more enzyme(s) of the kynurenine-nicotinic acid pathway downstream of an AlDH-inhibitory Trp metabolite, to increase the levels of the AlDH-inhibitory metabolites listed in (1) above and, in particular, use of tryptophan in association with an inhibitor of kynureninase, to increase levels of these AlDH inhibitors.

Accordingly, in another aspect, this invention provides a method of treating a patient in need thereof, which method comprises administration to the patient of a therapeutically effective amount of a compound selected from: (a) Trp, a Trp metabolite, and analogues and derivatives thereof (as defined herein) and (b) bioprecursors thereof (as defined herein), and (c) potentiators of (a) and/or (b) (as defined herein). Particularly, there is provided a method of treating alcoholism and alcohol dependence, which method comprises administering to a mammal in need thereof a therapeutically effective amount of one or more metabolite(s) of tryptophan or an analogue or derivative thereof, thereby to induce an aversion to alcohol and/or a reduction in alcohol consumption or craving.

In mammalian liver, AlDH exists in two main forms: the mitochondrial (or low $k_m$) and the soluble (or high $k_m$) form. The mitochondrial or low $k_m$ is responsible for oxidation of acetaldehyde after alcohol consumption in small to moderate amounts, e.g. as in social drinking, and is therefore the form whose inhibition is desirable in alcoholism aversion therapy. Therefore, the dosage is preferably an amount sufficient to exert a substantial inhibition of at least the low $k_m$ AlDH activity.

A wide range of tryptophan metabolites are possible candidates, but the following have shown particularly potent inhibition of AlDH activity:-3-hydroxykynurenine, 3-hydroxyanthranilic acid, kynurenic acid and indol-3-ylpyruvic acid. Although indol-3-ylpyruvic acid is known for use in treating anxiety and sleep disorders, none of the other metabolites have previously been proposed for use in medicine.

Accordingly, this invention further provides use of a compound selected from tryptophan, a tryptophan metabolite, or an analogue or derivative thereof (as defined herein), other than indol-3-ylpyruvic acid, in therapy.

Therapeutically active derivatives and analogues of these compounds may also be used. In the context of this invention, the term 'analogue' means a compound preparable by modifying a Trp metabolite by adding a substituent normally absent but that confers AlDH inhibitory activity to the compound; and the term 'derivative' means a compound preparable from either a Trp metabolite or an analogue thereof by replacing a substituent group with another or further substituent group. These include active derivatives of any of the above compounds in which the 3-hydroxy group of the tryptophan metabolite is replaced by a nucleophilic group, such as halo (eg chloro) and alkoxy, or other hydrophilic groups, or other substituent groups, such as lower ($C_{1-6}$) alkyl (eg methyl), or any of these group(s) substituted at one or more other position(s) (than the 3-hydroxy group).

Such derivatives and analogues are novel compounds. Accordingly, the present invention further provides use of a Trp metabolite producible by a metabolic pathway selected from the: kynurenine-nicotinic acid; serotonin; tryptamine or decarboxylation; and transamination metabolic pathways. Such novel compounds may be prepared by methods analogous to those known to those skilled in the art, such as from the corresponding known Trp metabolites. Accordingly, the present invention further provides use of Trp or a metabolite thereof in the preparation of a compound selected from:

(a) 3-hydroxy analogues of tryptophan metabolites normally absent a 3-hydroxy group in the benzene ring, other than 3-hydroxykynurenine and 3-hydroxyanthranilic acid; and (b) derivatives of: a compound selected from those defined in (a) and of 3-hydroxykynurenine, 3-hydroxyanthranilic acid, kynurenic acid and indol-3-ylpyruvic acid, in which compound:

(i) the 3-hydroxy group thereof of is replaced by substituent group selected from: nucleophilic groups, such as halo (eg chloro) and alkoxy, and other hydrophilic groups, and other substituent groups, such as lower ($C_{1-6}$) alkyl (eg methyl), and/or (ii) one or more other position(s) (than the 3-hydroxy group) are substituted by any of these substituent group(s).

In another aspect of the invention, there is provided a method of treating alcoholism and alcoholic dependence, which method comprises administering to a mammal a therapeutically effective amount of one or more inhibitor(s) of one or more enzyme(s) of the kynurenine-nicotinic acid pathway, either alone or in association with other substance(s), thereby to increase the levels of one or more of the tryptophan metabolite(s) which inhibit AlDH activity.

Preferably, said one or more inhibitor(s) inhibits the activity of kynureninase, for example, isoniazid, benserazide, o-methoxybenzoylalanine, and/or the activity of kynurenine hydroxylase, for example, m-nitrobenzoylalanine.

In another aspect, there is provided a method of treating alcoholism and alcoholic dependence, which method comprises administering to a mammal a therapeutically effective amount of tryptophan in association with one or more inhibitor(s) of one or more enzyme(s) of the kynurenine-nicotinic acid pathway, thereby to inhibit AlDH activity.

In another aspect, the present invention provides a pharmaceutical formulation comprising a compound selected from:

(a) an AlDH-inhibitory amount of a Trp metabolite, or an analogue or derivative thereof (as defined herein) or (b) a bioprecursor thereof (as defined herein), or (c) a potentiator of (a) and/or (b) (as defined herein) in association with a pharmaceutically acceptable carrier therefor. Preferably, there is provided a pharmaceutical composition comprising an AlDH-inhibitory amount of one or more tryptophan metabolite(s) or active analogue(s) or derivative(s) thereof and a pharmaceutically acceptable carrier therefor. Preferably, the tryptophan metabolites are selected from: 3-hydroxykynurenine, 3-hydroxyanthranilic acid, kynurenic acid and indol-3-ylpyruvic acid and derivatives thereof.

In yet another aspect, there is provided a pharmaceutical composition comprising a therapeutically active amount of one or more inhibitor(s) of the kynurenine-nicotinic acid pathway and a pharmaceutically acceptable carrier therefor.

As well as AlDH-inhibitory Trp metabolites, (or bioprecursors or potentiators thereof), the formulations, uses and methods of this invention may comprise one or more other active agents in association therewith, or may comprise more than one Trp metabolite (or bioprecursors or potentiators thereof) in association with each other. In the context of this invention, 'in association with' means that the formulation, use or method is adapted for simultaneous, sequential or concurrent use or administration, whether in admixture together or in separate formulations or compositions or in any other manner known to those skilled in the art.

In another aspect, there is provided a pharmaceutical composition comprising a therapeutically effective amount of tryptophan in association with a therapeutically effective amount of one or more inhibitor(s) of the kynurenine-nicotinic acid pathway, and one or more pharmaceutically acceptable carrier(s) therefor.

Preferably, said inhibitor is an inhibitor of kynureninase or kynurenine hydroxylase, such as one of those mentioned hereinbefore.

In a further aspect, there is provided a pharmaceutical composition comprising a therapeutically active amount of tryptophan or a metabolite or derivative thereof in association with an alcoholism relapse-treatment drug, such as acamprosate (calcium acetyl-homotaurinate, also known as Campral), optionally further in association with one or more inhibitors) of an enzyme(s) of the kynurenine-nicotinic acid pathway. Preferably, said inhibitor is an inhibitor of kynureninase and/or tryptophan-2,3-dioxygenase (also known as tryptophan pyrrolase).

In another aspect, there is provided a pharmaceutical composition comprising a therapeutically active amount of tryptophan or a metabolite or derivative thereof in association with an alcoholism relapse- or extinction-treatment drug, such as naltrexone, or a pharmacologically effective analogue or derivative thereof, optionally further in association with one or more inhibitor(s) of an enzyme(s) of the kynurenine-nicotinic acid pathway. Preferably, said inhibitor is an inhibitor of at least one of kynureninase and tryptophan-2,3-dioxygenase (also known as tryptophan pyrrolase).

In yet another aspect, there is provided a pharmaceutical composition comprising a therapeutically active amount of tryptophan or a metabolite or derivative thereof in association with an alcoholism relapse- or extinction-treatment drug, such as nalmefene or a pharmacologically effective analogue or derivative thereof, optionally further in association with one or more inhibitor(s) of enzyme(s) of the kynurenine-nicotinic acid pathway. Preferably, said inhibitor is an inhibitor of at least one of kynureninase and tryptophan-2,3-dioxygenase (also known as tryptophan pyrrolase).

In a further aspect, there is provided a pharmaceutical composition comprising a therapeutically active amount of tryptophan in association with an alcoholism relapse- and/or extinction-treatment drug, such as acamprosate (also known as Campral) and naltrexone or a pharmacologically effective analogue or derivative thereof, optionally further in association with one or more inhibitor(s) of enzymes of the kynurenine-nicotinic acid pathway. Preferably, said inhibitor is an inhibitor of at least one of kynureninase and tryptophan-2,3-dioxygenase (also known as tryptophan pyrrolase).

In yet a further aspect, there is provided a pharmaceutical composition comprising a therapeutically active amount of tryptophan in association with an alcoholism relapse- and/or extinction-treatment drug, such as acamprosate (also known as Campral) and nalmefene or a pharmacologically effective analogue or derivative thereof, optionally further in association with one or more inhibitor(s) of enzyme(s) of the kynureninase-nicotinic acid pathway. Preferably, said inhibitor is an inhibitor of at least one of kynureninase and tryptophan-2,3-dioxygenase (also known as pyrrolase).

In another aspect, there is provided a method of treating alcoholism and alcoholic dependence, comprising administering to a mammal in need thereof a therapeutically effective amount of a composition as described above.

The invention also extends to the use of the compositions or compounds described above in the preparation of a medicament for treating alcoholism and/or alcohol dependence.

The tryptophan metabolite(s) or bioprecursor or potentiator thereof can be administered by any conventional means available for use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice.

The dosage administered will, of course, vary depending on the use and known factors such as the pharmacodynamic characteristics of the particular agent, and its mode and route of administration; age, health, and weight of the recipient; nature and extent of symptoms, kind of concurrent treatment, frequency of treatment, and the effect desired. The recipient may be any type of mammal, but is preferably a human.

For use in the treatment of diseases characterized by abnormally high consumption of alcohol, by way of general guidance, a daily oral dosage of active ingredient(s) can be about 0.001 to 1000 mg/kg of body weight. Ordinarily a dose of 0.1 to 500 mg/kg per day in divided doses one to four times a day or in sustained release form is effective to obtain the desired results. The proper dosage of the composition in this invention will be readily ascertainable by a medical practitioner skilled in the art, based upon the present disclosure. By way of general guidance, typically a daily dosage may be about 10 milligrams to about 1.5 grams of each component.

In the methods and uses of the present invention, the compounds herein described in detail can form the active ingredient, and are typically administered in a mixture with suitable pharmaceutical diluents, excipients, or carriers (collectively referred to herein as a carrier or carrier materials) suitably selected with respect to the intended form of administration and consistent with conventional pharmaceutical practices.

Dosage forms (compositions) suitable for administration contain about 1 milligram to 100 milligrams of active ingredient per unit. In these pharmaceutical compositions, the active ingredient will ordinarily be present in an amount of about 0.5-95% by weight based on the total weight of the composition.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and colouring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Gelatin capsules generally contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be a coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and crosslinked or amphipathic block copolymers of hydrogels.

Liquid dosage forms for oral administration can contain colouring and flavouring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilising agent, and, if necessary, buffer substances. Anti-oxidizing agents such as sodium bisulphate, sodium sulphite or ascorbic acid, either alone or combined, are suitable stabilising agents. Also used are citric acid and its salts and sodium EDTA. In addition, parenteral solutions can contain preservatives, such as benzalkonium chloride, methyl- or propyl-paraben, and chlorobutanol.

The compounds for the present invention can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The invention also extends to any inventive combination of the features set out hereabove or in the following Examples.

The invention will be better understood from the following description and non-limiting Examples.

EXAMPLE 1

Results of Screening of Tryptophan Metabolites for Inhibition of AlDH Activity

Tryptophan and its various metabolites were tested for possible inhibition of activity of AlDH of bacterial sources. The terms "inhibitor of AlDH activity" and the like mean that the activity of AlDH in vivo in the presence of the inhibitor is reduced. In practice, this may be predicted by reference to the inhibitory activity of the compound or composition in vitro. A substance or composition which exhibits inhibition of less than 20% at 100 µM concentration is deemed poor. Those with inhibitions of between 20-56% are deemed moderate-good, and those with inhibitions of greater than 60% as good.

An enzyme preparation was purchased from Sigma, (Poole, Dorset, UK) and was used for the screening of tryptophan and its metabolites. A number of preliminary experiments were performed to optimise the conditions of the assay, which was performed according to standard experimental conditions published in the literature and well known to those skilled in the art. All assays were performed in triplicate or quadruplicate determinations for both controls (no additions) and tryptophan metabolites.

Tryptophan and its metabolites were first tested at a 100 µM concentration. The tryptophan metabolites screened included the following:

(1) Metabolites of the kynurenine-nicotinic acid pathway: these were kynurenine, 3-hydroxykynurenine, 3-hydroxyanthranilic acid, anthranilic acid, xanthurenic acid, kynurenic acid, quinolinic acid, quinaldic acid, α-ketoadipic acid, and nicotinamide.

(2) Metabolites of the serotonin pathway: these were 5-hydroxytryptophan, serotonin (i.e. 5-hydroxytryptamine), 5-hydroxyindol-3-ylacetic acid, and 5-hydroxytryptophol.

(3) Metabolites of the tryptamine or decarboxylation pathway: these were tryptamine, indol-3-ylacetaldehyde, and indol-3-ylacetic acid.

(4) Metabolites of the transamination pathway: there was only one such metabolite, indol-3-ylpyruvic acid.

(5) Other complex metabolites: these were harman and norharman.

The following results were obtained, which are given below for groups of metabolites according to extent of inhibition.

Inactive or Poor Inhibitors (i.e. Producing Inhibition of Less Than 20%)

These were the following (with their % inhibition of AlDH activity shown in parentheses): tryptophan (2%), quinolinic acid (13%), quinaldic acid (7%), anthranilic acid (9%), α-ketoadipic acid (1%), nicotinamide (7%), 5-hydroxytryptamine (serotonin) (15%), 5-hydroxyindol-3-ylacetic acid (4%), 5-hydroxytryptophol (7%), tryptamine (0%) and indol-3-ylacetic acid (11%). Under the same experimental conditions, the well-known AlDH inhibitor disulfiram produced a 95% inhibition at a similar (100 µM) concentration. From these data, it appears that neither tryptophan itself nor the above metabolites cause any significant inhibition of AlDH activity in vitro and are therefore unlikely to exert a significant effect in vivo. Even the strongest inhibitor, serotonin, is unlikely to exert a significant effect as its levels in vivo are unlikely to reach 100 µM.

Moderate-Good Inhibitors (i.e. Producing a 20-56% Inhibition)

The following tryptophan metabolites produced a moderate-good degree of inhibition of bacterial AlDH activity in vitro when tested at a 100 µM concentration: kynurenine (24%), xanthurenic acid (56%), 5-hydroxytrytophan (23%), indol-3-ylacetaldehyde (55%), harman (18%) and norharman (23%), all against a 95% inhibition by the classic AlDH inhibitor disulfiram at the same concentration (100 µM). Here, again, it is generally unlikely that these metabolites could accumulate at this level to cause inhibition of AlDH activity in vivo, except perhaps xanthurenic acid under certain conditions.

Strong Inhibitors (i.e. Those Causing Inhibition Greater Than 60%)

The following tryptophan metabolites produced a strong inhibition of bacterial AlDH activity in vitro when tested at a 100 µM concentration: 3-hydroxykynurenine (97%), 3-hydroxyanthranilic acid (97%), kynurenic acid (90%), indol-3-ylpyruvic acid (94%), against a 95% inhibition by disulfiram at the same concentration (100 µM) disulfiram.

EXAMPLE 2

Strong Inhibitors Tested at Smaller Concentrations

The strong inhibitory tryptophan metabolites were then tested at two smaller concentrations: 10 µM and 2 µM.

The above four inhibitory tryptophan metabolites were tested for inhibition of bacterial AlDH activity at the smaller concentrations of 10 µM and 2 µM against the same concentrations of disulfiram. At 10 µM, inhibition was as follows: 3-hydroxykynurenine (55%), 3-hydroxyanthranilic acid (17%), kynurenic acid (30%) and indol-3-ylpyruvic acid (29%), against a 99% inhibition by a 10 µM disulfiram. When these tryptophan metabolites were tested at a 2 µM concentration, only indol-3-ylpyruvic acid caused a significant inhibition of bacterial AlDH activity, of 24%. The other three metabolites exerted no significant effect (+1%, 3% and 5% for 3-hydroxykynurenine, 3-hydroxyanthranilic acid and kynurenic acid respectively). Under the same experimental conditions, disulfiram (at 2 µM) caused a 72% inhibition of AlDH activity.

EXAMPLE 3

Further Experiments with Tryptophan Metabolites Using the Mammalian Mitochondrial or Low $k_m$ AlDH The effects of tryptophan metabolites on activity of AlDH from a mammalian source, namely rat liver, have been tested using a preparation from rat liver containing both Low $K_m$ and high $K_m$ AlDH and assayed under the same protocol in Example 1. Preliminary results from testing the possible inhibition of low $k_m$ enzyme show that the four tryptophan metabolites which caused the strongest inhibition of the bacterial enzyme (namely 3-hydroxykynurenine, 3-hydroxyanthranilic acid, kynurenic acid and indol-3-ylpyruvic acid) are all strong inhibitors of the activity of the mammalian low $k_m$ enzyme, causing 65%, 46%, 30% and 37% inhibition respectively at the small 2 µM concentration level. Under the experimental conditions, disulfiram caused 30-46% inhibition of the low $k_m$ enzyme at a 2 µM concentration. These results are very encouraging indeed and suggest that tryptophan metabolites may be strong inhibitors of the low $k_m$ or mitochondrial form of AlDH and thus potential alcoholism aversion therapeutic agents.

Conclusion

From the above results, a number of further conclusions and comments could be made. The first concerns the inhibitory activity. Since 3-hydroxykynurenine and 3-hydroxyanthranilic acid are more potent AlDH inhibitors than their non-hydroxylated derivatives kynurenine and anthranilic acid respectively, it may be concluded that the presence of a hydroxyl group in the third position of the benzene ring confers inhibition or strong inhibition. It is possible also that other substituents at position 3 (e.g. chloro or other halo) and/or (an) additional position(s) may confer inhibition or a stronger inhibition.

Secondly, since there was no significant inhibition by tryptophan, tryptamine, 5-hydroxytryptamine or its metabolites 5-hydroxyinol-3-ylacetic acid and 5-hydroxytryptophol, it may be concluded that neither the indole structure, nor its hydroxylation in the 5-position or the presence of a side-chain amino group confer inhibition.

Thirdly, aldehydic metabolites, such as indol-3-ylacetaldehyde, are good inhibitors, almost certainly by virtue of being potential competitors with acetaldehyde for the enzyme. However these are likely to be of less therapeutic use since they may oxidise to the corresponding acid in vivo.

EXAMPLE 4

Confirmatory in vivo Tests

Further experiments were performed to establish whether the four strongly inhibiting compounds and other Trp metabolites are capable of inhibiting the form of AlDH responsible for oxidation of acetaldehyde in vivo in the mammalian liver, namely the mitochondrial enzyme or the so-called low $K_m$ enzyme.

Experiments were therefore performed using a preparation from rat liver in which both the low $K_m$ and the high $K_m$ enzymes can be measured simultaneously, but at different substrate (acetaldehyde) concentrations, namely, 5 µM for the low $K_m$ and 5 mM for the high $K_m$, enzyme.

A screening of the whole range of Trp metabolites and Trp itself, as in Example 1, revealed that, of all Trp metabolites tested on the mammalian enzyme, the above four metabolites (3-hydroxykynurenine, 3-hydroxyanthranilic acid, kynurenic acid and indol-3-ylpyruvic acid) were again the most potent inhibitors of the low $K_m$ enzyme. Thus, at a 100 µM concentration, these four metabolites caused a significant inhibition of 69%, 76%, 43% and 53%, respectively, in comparison with an inhibition by a 100 µM concentration of the classical inhibitor disulfiram of 46-50%. At a 10 µM concentration, the inhibition of activity of the low $K_m$ enzyme by the above four Trp metabolites was 52%, 54%, 43% and 38%, respectively, against an inhibition by a 10 µM concentration of disulfiram of 38-43%. Finally, at a 2 µM concentration, inhibition by the above four Trp metabolites was 55%, 46%, 40% 30% respectively, against an inhibition by a 2 µM concentration of disulfiram of 30-46%.

From these data, it is clear that the four AlDH-inhibitory Trp metabolites listed above, namely 3-hydroxykynurenine, 3-hydroxyanthranilic acid, kynurenic acid and indol-3-ylpyruvic acid, are equally as strong, or even stronger, inhibitors of the low $K_m$ enzyme from rat liver mitochondria compared with the currently-used aversion-therapeutic drug disulfiram. Inhibition of the low $K_m$ enzyme is an important pre-requisite for an effective alcoholism aversion therapeutic agent, and the present results therefore not only support and strengthen the earlier findings, but also provide strong support to the validity of proposing these Trp metabolites as potential alcoholism-aversion therapeutic agents.

The invention claimed is:

1. A method of treating alcoholism and/or alcohol dependence via alcohol aversion therapy, said method comprising administering by an oral administration route to a subject in need thereof a therapeutically effective amount of:
   a Trp metabolite chosen from 3-hydroxykynurenine or 3-hydroxyanthranilic acid,
   to thereby inhibit activity of the enzyme aldehyde dehydrogenase (AlDH).

2. A method of treating alcoholism and/or alcohol dependence via alcohol aversion therapy, said method comprising administering to a patient in need thereof a therapeutically effective amount of a tryptophan (Trp) metabolite chosen from a derivative of 3-hydroxykynurenine or a derivative of 3-hydroxyanthranilic acid, in which the 3-hydroxy group of the 3-hydroxykynurenine or the 3-hydroxyanthranilic acid is replaced by a substituent group selected from the group consisting of halo, alkoxy, and lower ($C_{1-6}$) alkyl, to thereby inhibit activity of the enzyme aldehyde dehydrogenase (AlDH).

3. The method according to claim 1, wherein the therapeutically effective amount of Trp metabolite is divided into one to four daily doses.

4. The method according to claim 2, wherein the therapeutically effective amount of Trp metabolite is divided into one to four daily doses.

* * * * *